Figure 1:
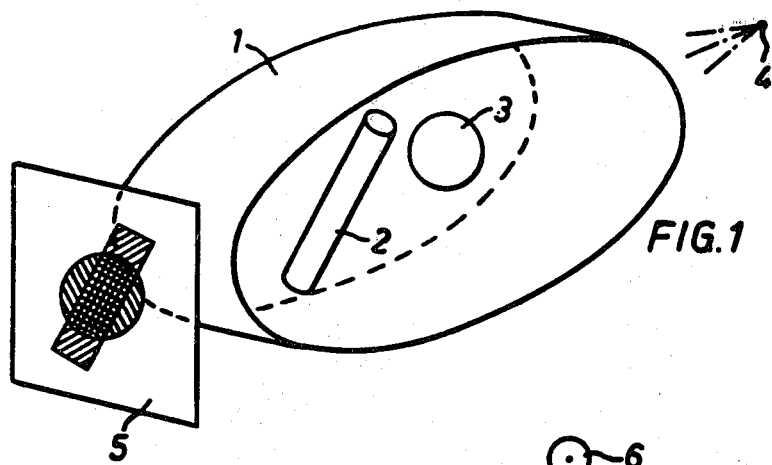
Figure 2A:
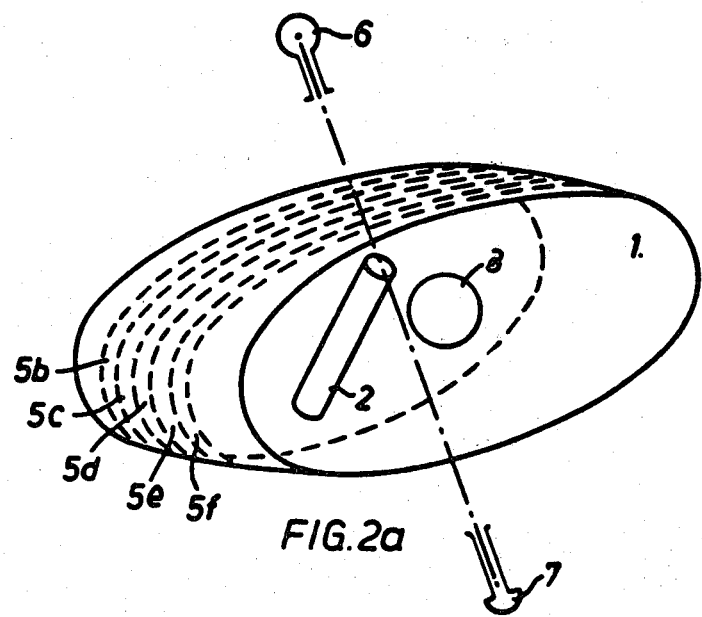
Figure 2B:
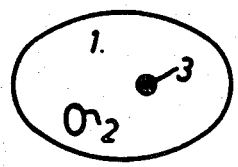
Figure 2C:
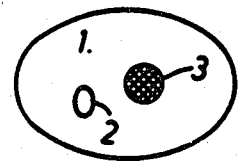
Figure 2D:
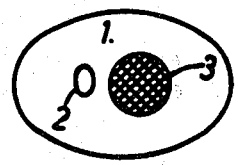
Figure 2E:
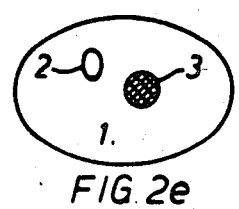
Figure 2F:
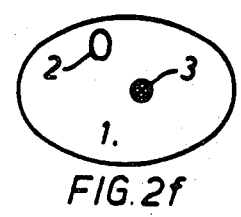

United States Patent [19]

Hounsfield

[11] 4,399,509
[45] * Aug. 16, 1983

[54] APPARATUS FOR EXAMINING A BODY BY RADIATION SUCH AS X OR GAMMA RADIATION

[75] Inventor: Godfrey N. Hounsfield, Newark, England

[73] Assignee: EMI Limited, Hayes, England

[*] Notice: The portion of the term of this patent subsequent to Dec. 11, 1990, has been disclaimed.

[21] Appl. No.: 93,123

[22] Filed: Nov. 13, 1979

Related U.S. Application Data

[60] Division of Ser. No. 858,612, Dec. 8, 1977, Pat. No. 4,188,541, which is a division of Ser. No. 780,971, Mar. 24, 1977, abandoned, which is a continuation of Ser. No. 657,543, Feb. 12, 1976, Pat. No. 4,052,618, which is a division of Ser. No. 468,005, May 7, 1974, Pat. No. 3,944,833, which is a division of Ser. No. 349,198, Apr. 9, 1973, Pat. No. 3,866,047, which is a continuation-in-part of Ser. No. 212,778, Dec. 27, 1971, Pat. No. 3,778,614, which is a continuation of Ser. No. 861,358, Aug. 21, 1969, abandoned.

[30] Foreign Application Priority Data

Aug. 23, 1968 [GB] United Kingdom ............. 40317

[51] Int. Cl.³ .............................................. G06F 15/42
[52] U.S. Cl. ................................. 364/414; 378/4; 378/21; 378/901
[58] Field of Search .............. 364/414; 250/445 R, 250/445 T; 358/110, 111; 378/901, 21, 8, 11-14, 21

[56] References Cited

U.S. PATENT DOCUMENTS 2,281,931  0/1942  Frank ............................ 250/61.5
3,106,640  0/1963  Oldendorf ..................... 250/52
3,158,744  11/1964  Bernstein ...................... 250/490
3,432,657  3/1969  Slavin .......................... 250/490

OTHER PUBLICATIONS

Kalos; "Conceptual Design of a Vapor Volume Fraction Instrument", AEC Contract at (30-1)-2303(IX), Apr. 1961.

Kuhl et al., "Transmission Scanning a Useful Adjunct to Conventional Emission Scanning for Accuractely Keying Isotype Depositon to Radiographic Anatomy", 87 Radiology 278 (1966).

Takahashi, S. (1957), Rotation Radiography, Japan Society for Promotion of Science, Tokyo.

Takahashi, S. (1969), "An Atlas of Axial Transverse Tomography and its Clinical Application, "Springer Verlag, Berlin.

Cormack, A. M. (1963), "Representation of a Function by its Line Integrals, with Some Radiological Applications, " Journal of Applied Physics, 34, 2722–2727.

Cormack,. A. M. (1964), "Representation of a Function by Its Line Integrals, With Some Radiological Applications," II Journal of Applied Physcis, 35, 2980–2913.

Kuhl, D. E. & Edwards, R. Q. (1964), "Cylindrical and Section Radioisotope Scanning of the Liver and Brain," Radiology 83 (5). 926–936.

Kuhl, D. E. & Edwards, R. Q. (1966), "Perforated Tape Recorder for Digital Scan Data Store With Grey Shade and Numeric Readout", Journal of Nuclear Medicine 7, 269–280.

Kuhl, D. E. & Edwards, R. Q. (1968), "Digital Techniques for On-Site Scan Data Processing," Fundamental Problems in Scanning, Charles C. Thomas, Springfield, Illinois, pp. 250–266.

Radon, Johann, Uber die Bestimmung von Funktionen durch ihre Integralwerte langs gewisser Manningfaltigkeiten, 1917 Sitzung Vom 262–277, w/Informal Translation: Determination of Functions by its Integral Values Along Various Defined Manifoldnesses.

Bracewell, R. N. & Roberts, J. A. (1954), "Aerial Smoothing in Radio Astronomy," Australian Journal of Physics 7(4), 615–640.

Bracewell, R. N. (1956), "Strip Integration in Radio Astronomy," Australian Journal of Physcis 9(2), 198–217.

Bracewell, R. N. (1964), "Reducing Fan Beam Data," Radio Astronomy Institute, Stanford University, Glint No. 76, Mar. 9, 8 pp.

Bracewell, R. N. & Riddle, A. C. (1967), "Inversion of Fan-Beam Scans in Radio Astronomy," Astrophys. Journal 150(2). 427–434.

DeRosier, D. J., Klug, A., Reconstruction of Three

Dimensional Structures from Electron Micrographs, 217 Nature 131 (1968).

*Primary Examiner*—Errol A. Krass

[57] ABSTRACT

A method of examining a patient with x-rays is described in which x-ray measurements are taken of the attenuation suffered by x-radiation when projected across a cross-sectional slice of a patient's body along each of many substantially linear beam paths and are subjected to compensated back-projective processing to produce an x-ray picture representing the variation of attenuation of the radiation with position over the slice. Beam paths which are next to each other in space are arranged to overlap each other.

68 Claims, 24 Drawing Figures

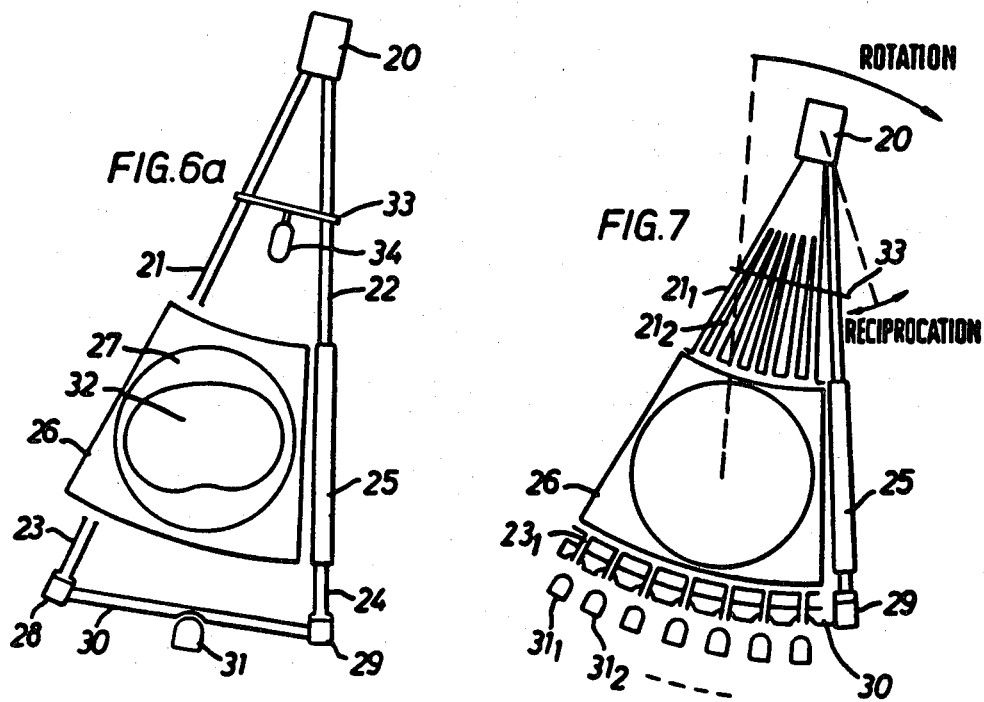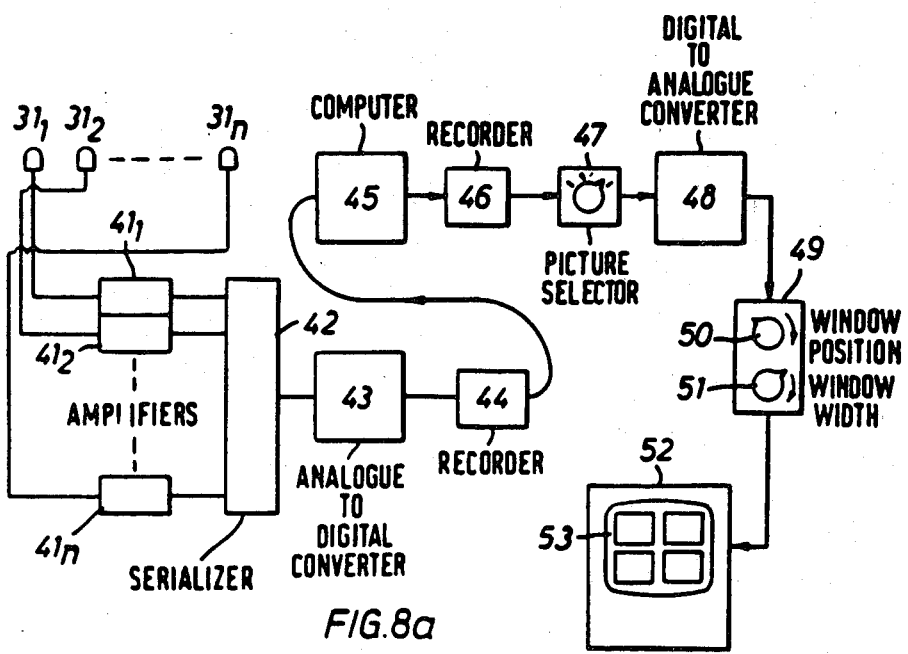

ABORTUS FOR EXAMINING A BODY BY
RADIATION SUCH AS X OR GAMMA RADIATION

This is a division, of application Ser. No. 858,612 filed 12-08-77, now U.S. Pat. No. 9,188,541, which is a division of Ser. No. 780,971 filed 03-24-77 (now abandoned); which is a continuation of Ser. No. 657,543 filed 02-12-76 (now U.S. Pat. No. 4,052,618); which is a division of Ser. No. 468,005 filed 05-07-74 (now U.S. Pat. No. 3,944,833); which is a division of Ser. No. 349,198 filed 04-09-73 (now U.S. Pat. No. 3,866,047); which is a continuation in part of Ser. No. 212,778 filed 12-27-71 (now U.S. Pat. No. 3,778,614); which is a continuation of Ser. No. 861,358 filed 08-21-69 (now abandoned).

The method and apparatus according to the invention can be used to produce radiographs in any convenient form, such as a picture on a cathode ray tube or other image forming device, a photograph of such a picture, or a map of absorption coefficients such as may be produced by a digital computer and on which "contours" may subsequently be drawn.

One object of the present invention is to provide apparatus for examining a sectional slice of a body by means of penetrating radiation in such a way that information can be obtained from a plurality of sets of rays following ray paths in said slice, the rays in one set being angularly spaced from those in another.

Another object of the invention is to provide an improved method of, and apparatus for, examining a body by means of penetrating radiation, and in which substantially no relative motion is required between a source of radiation and one or more radiation detectors.

Another object of the present invention is to provide an improved method of, and apparatus for, examining a body by means of penetrating radiation, whereby the examination can be carried out rapidly.

Figure 3:
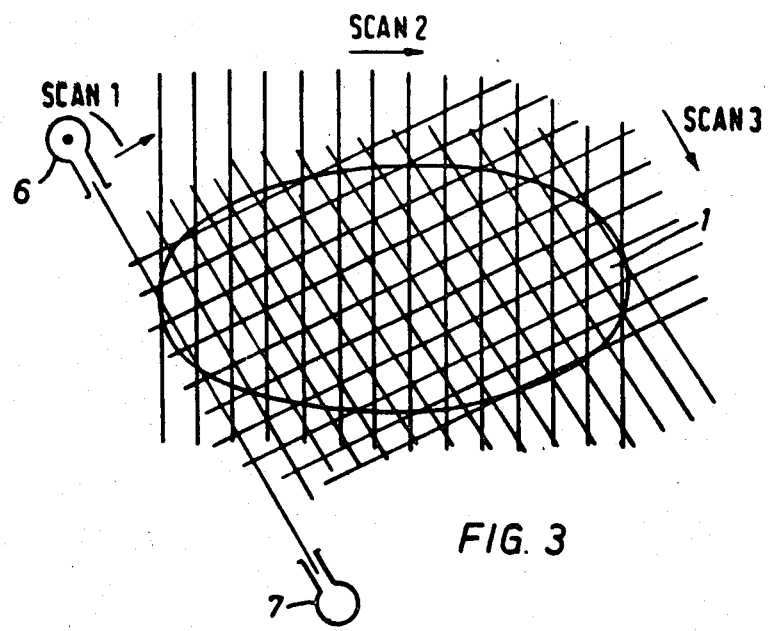
Figure 4:
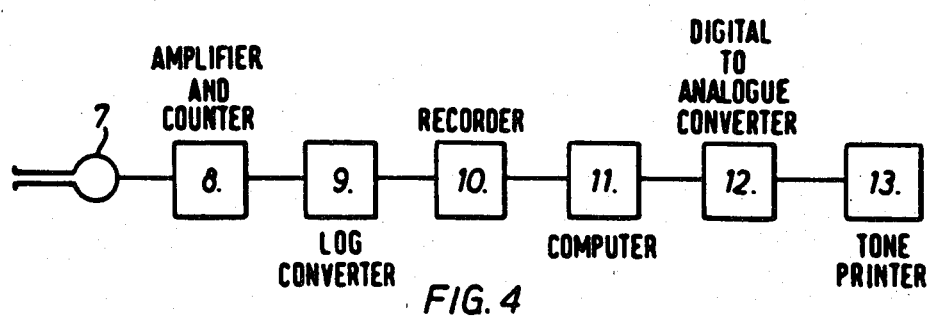
Figure 5:
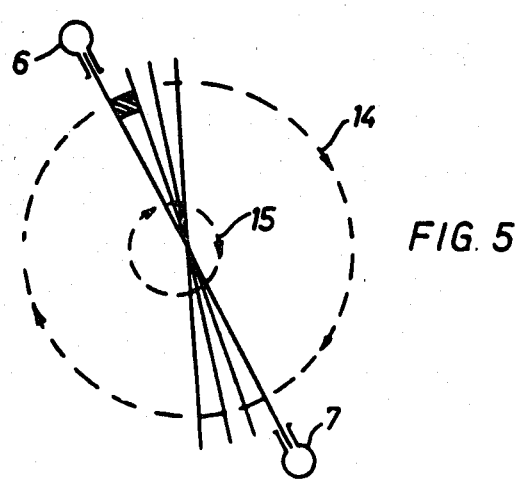
Figure 6B:
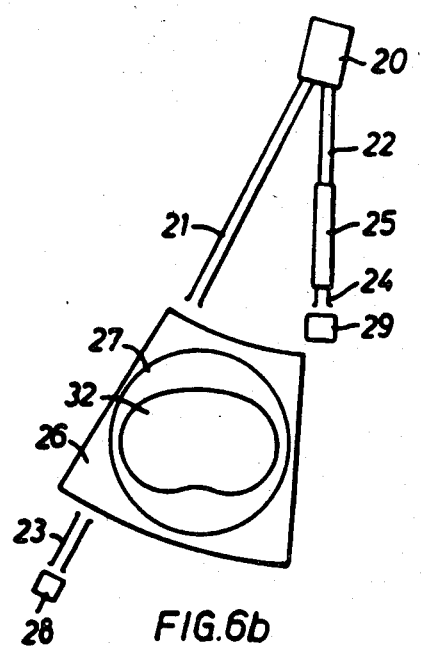
Figure 8B:
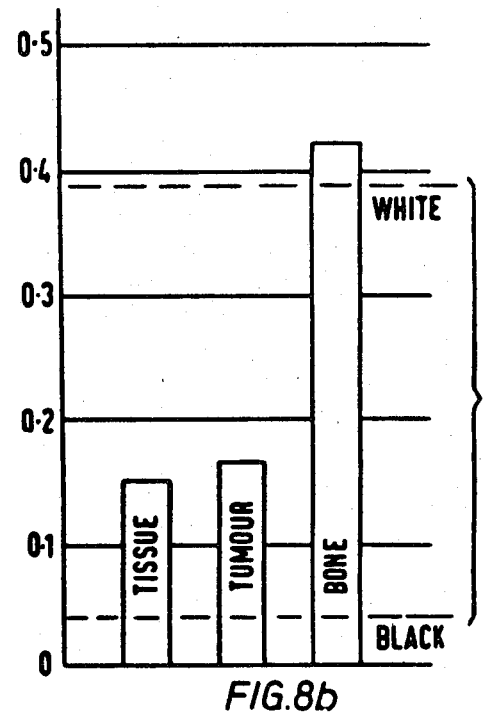
Figure 8C:
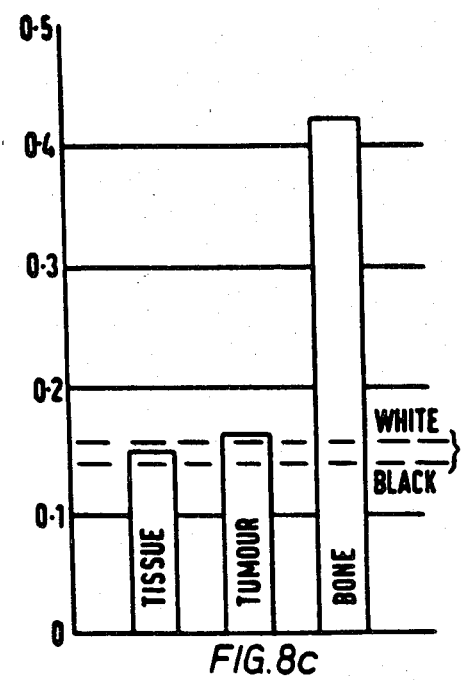
Figure 8D:
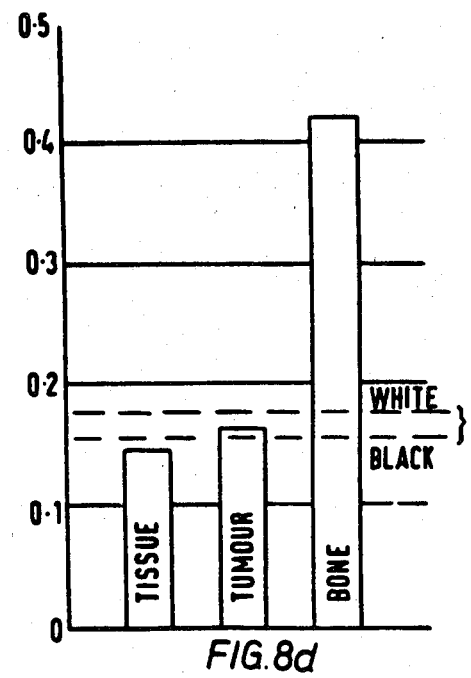
Figure 9A:
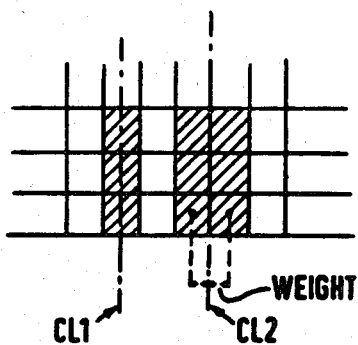
Figure 9B:
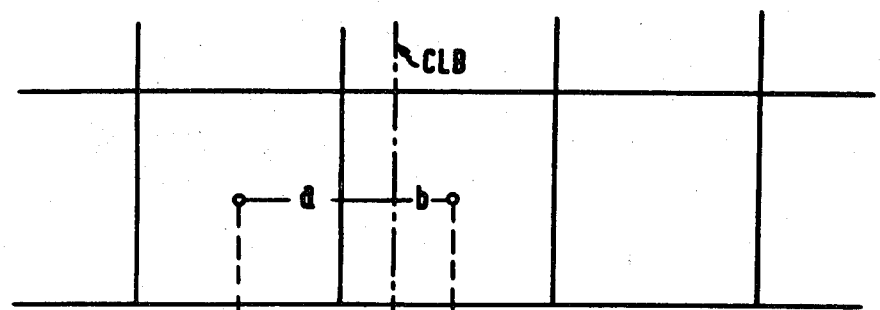
Figure 9C:
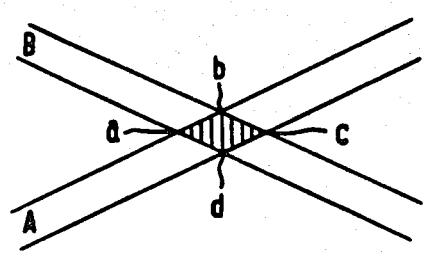
Figure 9D:
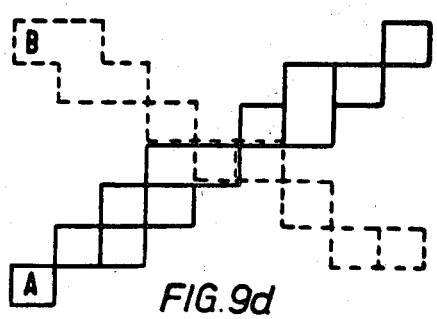
Figure 10:
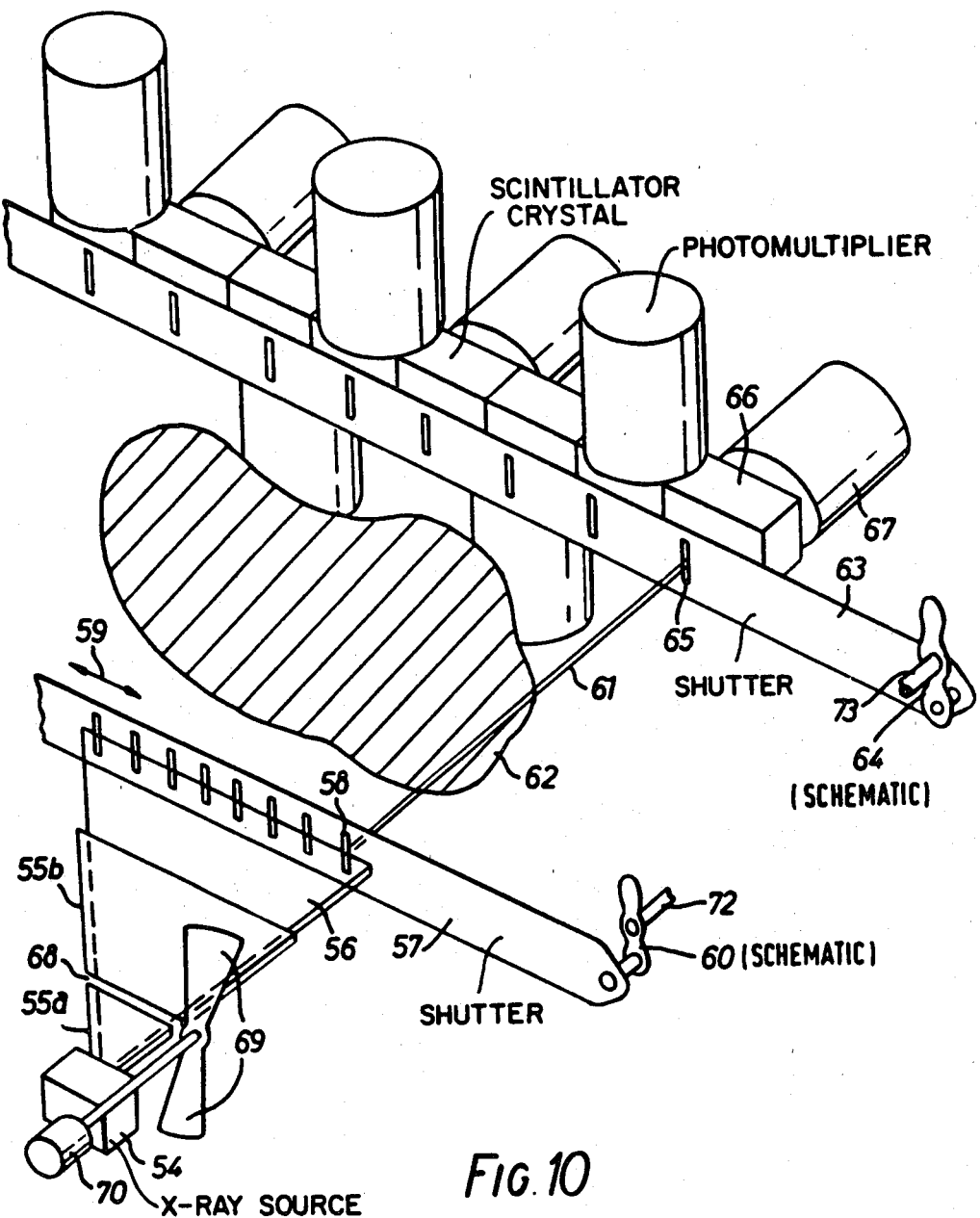
Figure 11:
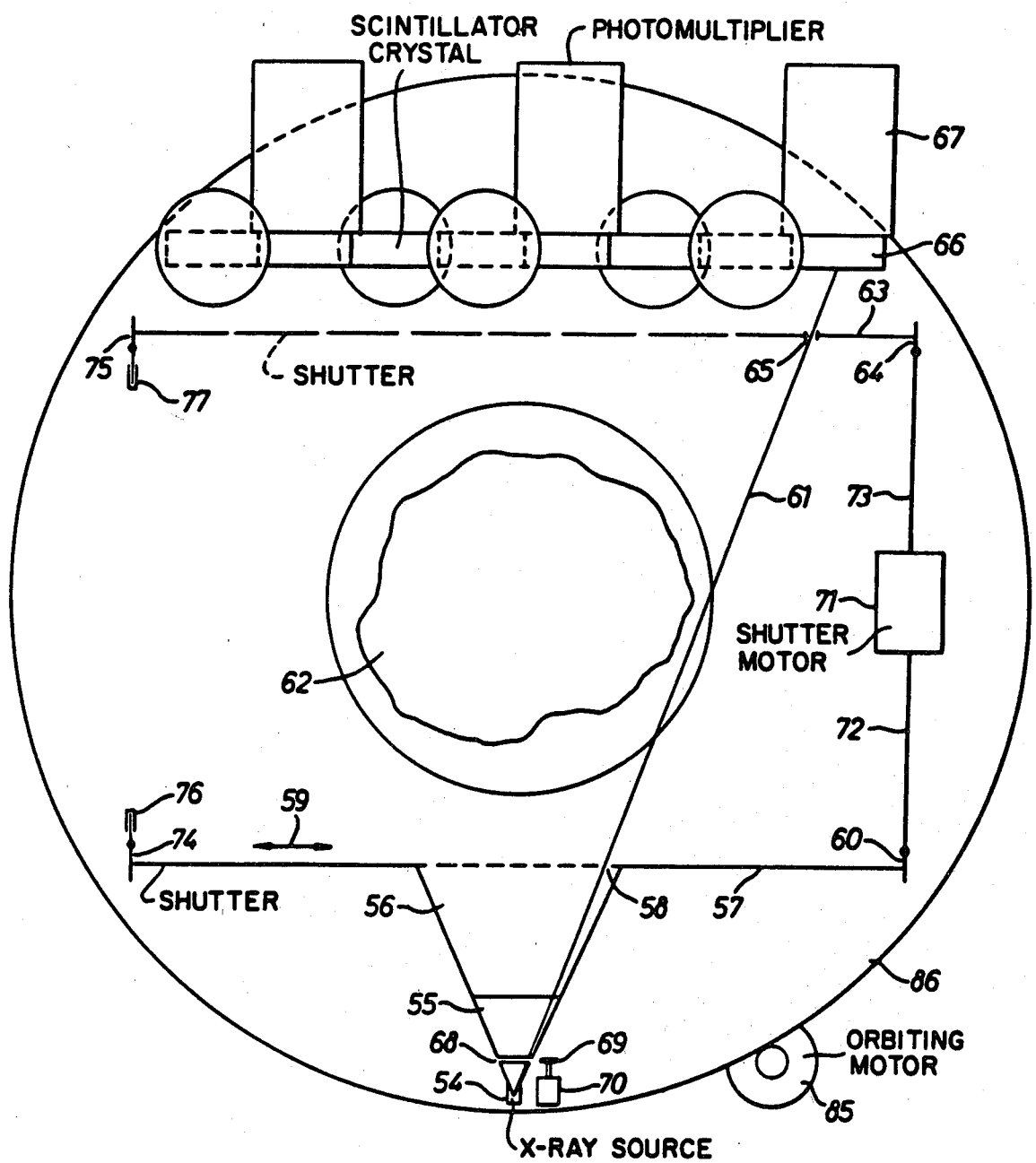
Figure 12:
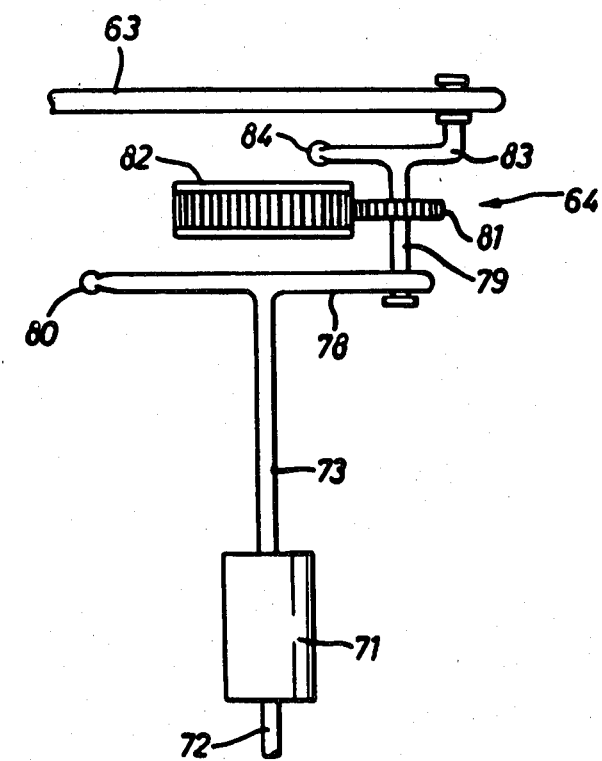

In order that the invention may be clearly understood and readily carried into effect, the same will now be described with reference to the accompanying drawings in which:

FIG. 1 shows the kind of picture produced by conventional X-ray apparatus,

FIGS. 2a, 2b, 2c, 2d, 2e, and 2f illustrate the principle of the technique claimed in my application Ser. No. 212,778 (now U.S. Pat. No. 3,778,614) and the kind of picture produced by said technique:

FIG. 3 shows one method of scanning used in the said technique,

FIG. 4 shows in block form suitable apparatus for carrying out the said technique, FIG. 5 shows an alternative method of scanning, FIGS. 6a and 6b illustrate diagrammatically the construction of the scanning means of apparatus according to two other examples of the said technique, FIG. 7 illustrates a modification of FIG. 6a, FIG. 8a illustrates, partly in block form, the apparatus embodying the scanning means illustrated in FIG. 7, FIGS. 8b, 8c and 8d are diagrams useful in explaining the operation of parts of the apparatus shown in FIG. 8a, FIGS. 9a, 9b, 9c and 9d illustrate the application of weighting factors to elements of the picture, FIG. 10 shows, in perspective view, apparatus according to another example of my invention, FIG. 11 shows the apparatus of FIG. 10 in plan view, and FIG. 12 shows in some detail part of an arrangement for driving the shutter members shown in FIGS. 10 and 11.

Referring to FIG. 1, this shows a body 1 containing a bone 2 and a tumour 3. Also shown are a source of X-rays 4 and an X-ray film 5. As can be seen, images of the bone and tumour are produced on the film, but partly superimposed. The tone of any point on the film is dependent on the product of the co-efficients of transmission of all the elements lying between that point and the X-ray source. Thus if the bone 2 has the lowest co-efficient of transmission, the tumour 3 the second lowest and the surrounding material the highest, the X-ray image comprises a dark patch where the bone and tumour are superimposed, a lighter patch due to the bone not superimposed on the tumour and a still lighter patch due to the tumour not superimposed on the bone. These are surrounded by a light area where neither bone nor tumour is present. Also as the difference between the co-efficients of transmission of tumour and normal tissue are small, the differences in tone between the different parts of the X-ray picture are slight and difficult to detect using such a method.

Referring now to FIG. 2, the body, bone and tumour are denoted by the same references as in FIG. 1. The X-ray source is replaced by a source 6 which may also be of gamma rays but is preferably of X-rays. It differs from source 4 in that it produces a beam of small cross section area or a ray as it might also be called, for example 3 m.m square or diameter, and preferably includes a collimator to reduce scatter of the rays. The X-ray film 5 has been replaced by a detector 7, which may be a scintillator counter and a scintillation counter and which preferably also includes a collimator. The body 1 is scanned by the beam in one plane only, the plane being 3 m.m thick in this example, in a direction not only linearly across the plane, but at a plurality of angles round the plane, the detector 7 being so mounted that it is always pointing towards the source 6. FIG. 3 illustrates the scanning in more detail. If only a single scan across the plane were performed, the result would merely be equivalent to a conventional X-ray picture of that plane, all the objects on a line between source 6 and detector 7 being superimposed. However by performing a large number of scans, sufficient information can be derived to enable the coefficient of absorption of the material in each 3 m.m cube of material in the plane to be calculated and the co-odinates of its position in the plane determined. Although only three scans are shown in FIG. 3 it will be appreciated that many more would be required in practice.

In each position of the beam the detector 7 determines the transmission of the line X radiation by a path of relatively small cross-sectional area through the body. The plane under examination is regarded as a two dimensional matrix of elements and the directions and numbers of the paths is such that each element of the matrix is intersected by a group of paths, which paths intersect different groups of elements.

From the transmissions by all the paths, a series of simultaneous equations is built up represented by the discrete output signals, derived from the radiation traversing all the respective paths and by means of a digital computer provides the absorption coefficient of each element of the matrix. The outputs of the computer may be used to produce a picture or other representation of the section in any convenient form. Successive parallel planes may be examined in this way, and a picture of each planar slice produced to build up a picture of the entire body or a larger section of it. The slices may be examined in sequence or simultaneously by using a number of X-ray sources and detectors in parallel. FIGS. 2b to 2f show the pictures resulting from examination of planar slices 5b to 5f of body 1.

FIG. 4 shows a block diagram of the apparatus for producing pictures from the outputs from detector 7. The output from detector 7 is applied to an amplifier and counter 8 which produces a digital output representing the number of counts in each reading. The output from 8 is converted to logarithmic form in a logarithmic converter 9 whose output is stored in a punched-tape or magnetic tape recorder 10 before being transmitted to a digital computer 11 for processing. The computer 11 produces for each 3 m.m cube of a planar slice of body 1 a digital number representing the absorption coefficient of the material within that cube. These digital numbers may be converted to analogue form in digital-to-analogue converter 12 and applied to a tone printer 13 to produce a picture. Alternatively, the computer outputs may be retained in digital form for comparison by pattern recognition techniques, with other digitised pictures.

To achieve the required result, the absorption along each path is deduced from the transmission by each path and a knowledge of the initial intensity of the beam or ray entering each path. The logarithmic converter 9 is used to provide a linear output so that the total absorption along a path is equal to the sum of the absorption in each small element along the path. Let 100 parallel paths be used for each of 400 directions spaced equally over 180°. The computer 11 has then 40,000 figures to process, each representing the total absorption along a given path. Consider the section divided into 100×100 similar meshes as on Cartesian graph paper. Each mesh represents an element of the body, but the term mesh will be used in the following mathematical consideration for convenience. The computer 11 is then programmed to give the absorption for each of the 10,000 meshes.

Consider a ray which passes through a set of n=100 meshes through none of which a ray has previously passed. Let the total absorption be Z dB. The computer then allocates a provisional value of Z/100 to each of the meshes. Now suppose that, at a later stage, a ray passes through another set of 100 meshes the absorption in some or all of these meshes having already been allocated. Let the sum of the figures already allocated be $Z_1$ whereas the new measurement gives a total absorption $Z_2$. It will be appreciated that $Z_1$ constitutes a reconstruction of the output signal $Z_2$ derived from the last approximations to the absorptions of the respective meshes. Then a correction $(Z_2-Z_1)/100$ is added to the figures already appearing in each of the meshes. This process is then continued for all the 40,000 rays. This process gives a rough approximation, but to obtain better accuracy, the computer must repeat it a number of times, say five.

Consider a single section of the body in the xy-plane in which the absorption per unit distance in dB at the point x, y is z Let $z=f(x,y)$.

Now consider a single set of rays all parallel to the y-axis and spaced equally by intervals $\Delta x$. The rays are arranged to have a width rather greater than $\Delta x$ so that some overlapping occurs. The optimum beam width is determined empirically. For mathematical purposes the change of absorption though any interval $\Delta x$ is assumed to be negligible. We now suppose that the section of the body to be examined is bounded on two sides by the x- and y-axes and is square in shape so that it can be divided into M elementary squares with edges parallel to the axes.

The complete total of rays can be divided into sets each of which consists of parallel rays or effectively parallel rays at a given angle or mean angle. The sets of discrete output signals derived from the rays in each set are treated in the computer in sequence. However, since there are only about 100×100 meshes and about 400 angles are employed within 180°, rays at neighbouring angles must include some of the same squares and their absorption will not, therefore, be independent. If the sets were therefrom taken in angular succession the lack of independence would clearly lead to a slower convergence than if they were independent.

The computer is therefore arranged, by programming, to take the different angular subsets in a pseudo random order with large angular gaps, of say 40°, between successive sets of rays. The sequence is intended to ensure that every angle is included, but not repeated, within the 400 directions. Rays close together in angle then appear far apart in the computer scanning sequence.

The accuracy of detection by detectors such as 7 is limited so that the raw data contain errors and therefore, as the complete cycle of 100×400 measurements is analysed 4 or 5 times by the computer, the resultant figures for the meshes tend to oscillate. It has been found that this can be avoided by multiplying the later corrections by a factor which is less than unity and falls steadily for successive cycles.

The procedure may be represented mathematically as follows. The true continuous distribution function is given by equation (1)

$$z=(f(x,y)) \tag{1}$$

Let the distribution function reached at some stage of the work be $$z'=g(x,y) \tag{2}$$

which is a discontinuous function since z' must have the same value over each mesh.

Now consider an arbitrary ray passing through n meshes. If $z_r$ is the mean value of z through the r th mesh and Z is the total absorption (or attenuation) of the ray in dB as measured $$Z = \sum_1^n z_r \tag{3}$$

The value of z' for each mesh will also be known from the previous work. If no ray has passed through a given mesh z' is put equal to zero.

The mean square error for all the meshes along the path of the ray will be written E where $$nE = \sum_1^n (z'_r - z_r)^2 \tag{4}$$

and it is required to choose new values $z_r''$ to replace $z_r'$ in order to minimise E.

There is no reason to favour one mesh rather than another, and therefore a constant C is added to $z_r'$ where C is independent of r and must be obtained from the additional information provided by Z. Hence $$z_r'' = z_r' + C \qquad (5)$$

Hence the new value of n E will be $$n E = \sum_{1}^{n} (z''_r - z_r)^2 = \sum_{1}^{n} (z'_r - z_r + C)^2 \qquad (6)$$

The minimum value of E is obtained were C is equal to the mean value of $z_r - z_r'$ or $$C = \frac{\sum_{1}^{n}(z_r - z'_r)}{n} = Z/n - \frac{\sum_{1}^{n} z'_r}{n} \qquad (7)$$

Hence $$z''_r = z'_r + Z/n - \frac{\sum_{1}^{n} z'_r}{n} \qquad (8)$$

In other words the correction applied is equal to the mean value of the error. If none of the n meshes has previously appeared all the $z_r'$ are put equal to zero so that $$z_r'' = Z/n \qquad (9)$$

In other words the attenuation is, at first, uniformly distributed among the meshes.

For the s th ray equation (8) becomes $$z''_{rs} = z'_{rs} + Z_s/n - \frac{\sum_{r=1}^{n} z'_{rs}}{n} \qquad (10)$$

If there is a total of S rays there will be a total of S equations for a complete cycle. If m is the number of rays in a set of parallel rays and N is the number of angles $$S = m N \qquad (11)$$

If α is the number of complete cycles used by the computer, the total number of ray operations is q S.

Since the number of rays S per cycle is several times the number of meshes M, the number S of equations will be several times the number M of independent equations.

Difficulties arise in finding a system which traces through the picture matrix an equivalent beam or ray as it has been called heretofore which has effectively constant width, and which also includes the correct number of picture elements along its length. Both of these requirements are essential for the accurate computer calculations which are to follow.

The two worst cases are shown in FIG. 9a, where in one case a beam centre line CL1 passes through the squares of the maxtrix perpendicularly and the centre line of the beam passes through the centre of the squares, in the other case the beam centre line CL2 passes between the squares. The latter case would add up to twice as many squares as the former, when the squares along the length of the beam are added up, and would clearly give an error of 2:1.

In order to overcome the above problem the values in each square are multiplied by a weighting factor which is a function of the distance from the centre of the square to the centre line of the beam, i.e., the squares of beam 2 in FIG. 9a would have a weighting factor of 0.5, the resulting sum of the numbers in the two beams then being equal.

FIG. 9b shows an intermediate position of the beam in which the distances from the centre line CLB of the beam to the centres of the two affected squares in the beam are 'a' and 'b' respectively. The corresponding weighting factors 'A' and 'B' can be read off the graph, and when these are added together they must for reasons indicated above add up to unity. Therefore it follows that the parts of the curves labelled 'x' must be drawn the inverse of the parts labelled 'y', if the beam and hence the weighting curve is to be considered symmetrical about its centre line.

It can be shown that one requirement for accurate summation of values of the matrix squares is idealised in FIG. 9c and its practical equivalent is shown in FIG. 9d using a matrix with a beam at the same angle.

In FIG. 9c the area abcd is obviously constant at any position of the intersection of the beams and is a function of the angle of intersection of the two beams A and B. In FIG. 9d the two equivalent beams vary in width from one to two squares and a constant area at intersection would be impossible without the use of weighting factors. It can be shown that for a given X-ray beam width there is one weighting curve which fulfils all the requirements. For example, if the squares contained at the intersection of the beams in FIG. 9d are multiplied by their respective weighting factors taken from this curve, they will produce a sum which is proportional to the area abcd in FIG. 9c. Any angle of intersection may be chosen and the beam in FIG. 9b may be intersected anywhere along its length for this condition to remain true.

The weighting factor curve can be split up into a table of approximately 20 values to which the computer can refer during calculations without substantially impairing the accuracy of the system.

In the example illustrated in FIG. 3 only a single detector 7 is indicated. If however a fan-shaped or strip beam of radiation is used, with a group of detectors each for receiving radiation transmitted by one of the paths of small cross sectional area, some correction may have to be made in solving the equations for the effect of Compton scatter but in many cases this can be avoided by adequate spacing of the detectors.

As was previously mentioned, the differences in absorption between different materials is very small. However, in accordance with the invention the contrast of the picture produced can be so arranged that the full black to white range represents only the small range of absorption values which is of interest.

It is essential in all X-ray apparatus to ensure that the patient does not receive an overdose of radiation. In this respect the use of a scintillator and a scintillation counter is advantageous as its efficiency and accuracy in detecting X-rays are several orders better than those of photographic film. The maximum detail obtainable in a picture is a function of the number of counts per reading received by the scintillation counter around the edge of the body. In view of the limitation on the permissible number of counts per reading, it would not be feasible to produce a picture having the same order of definition as a television picture when examining a living body, although a high definition picture of an inanimate object could be produced. Moreover, in examining living bodies, it is not normally necessary to have a high definition picture of the whole body. Apparatus according to the invention can be used to produce a picture which is of high definition in the area of immediate interest and of low definition in surrounding areas. For example, as shown in FIG. 5 the radiation source 6 and detector 7 may be arranged to perform a circular scan indicated by the arrow 15 round the edges of the body, which is so positioned that the area of interest is near the centre of the scan. By averaging the number of counts over a small angle of rotation, mean values of absorption for areas enclosed by the angle such as the area shown shaded, may be calculated. It is clear from FIG. 5 that near the edges of the body only a relatively small number of large area elements are being examined, whereas at the centre a large number of small area elements is examined. Consequently the resulting picture will have a high definition near the centre and a low definition towards the edges. In producing the picture, the points may conveniently be plotted in polar co-ordinates. As in the example of FIG. 3, a large number of scans is required to produce sufficient information. In the embodiment of FIG. 5, the additional scans may be produced by superimposing a slower rotary motion which shifts the axis of the main rotation so that the centre of the circle of the main scanning motion traces a circle of small diameter. This additional scanning motion produces the intersecting paths for each element of the matrix according to which the body is examined. The superimposed motion need not be circular and need not be confined to the centre circle. For example it could be a spiral starting at the edge of the outer circle progressing rapidly towards the center then performing a slow spiral in the region of the centre. It may be more complicated provided that it achieves the object of even coverage at the centre.

Referring to FIG. 6a of the drawing there is represented therein an X-ray tube 20 from which the rays, when the tube is operating, pass through two collimators 21 and 22. The collimator 21 is aligned with a further collimator 23 and the collimator 22 is aligned with a further collimator 24. Between collimator 22 and 24 is located a dummy attenuator 25. There is a gap between the collimators 21 and 23 for the location of the object to be X-rayed and in the example illustrated this gap is occupied by a plastics block 26 having a central aperture 27 for the body to be X-rayed. Two scintillators 28 and 29 are located at the ends of the collimators 23 and 24 respectively and these communicate optically via a light pipe 30 with a photomultiplier 31. A chopper 33 rotatable by an electric motor 34 is arranged to allow beams to pass through the collimators 21 and 22 only alternately to produce scintillations in the scintillators 28 and 29 for detection by the photomultiplier 31. When the apparatus is in use, the collimators 21 to 24, the atteuator 25, the scintillators 28 and 29, the light pipe 30 the photo multiplier 31, the chopper 33 and the motor 34 are oscillated through the angle subtended by the block 26. The apertures of the collimators 21 and 23 define a ray path traversing the body located in the aperture 27 and the oscillator causes this ray path to scan the angular extent of the oscillation. A planar slice of the body is thus exposed to a fan-shaped sweep of rays, radiating from source 20. The X-ray source 20 does not take part in this oscillation because it produces a beam wide enough to span the block 26. However, the whole equipment is arranged to rotate or orbit slowly about the body to be examined by X radiation, so that the body is exposed to successive fan-shaped sweeps from different angles. The body is represented by the outline 32.

The use of the scintillator 29 and the attenuator 25 provides a reference for the photo multiplier 31. The material of the attenuator 25 is selected to have similar absorption properties to the body 32 to be examined so that accurate transmission readings may be obtained from the X radiations which pass through this body substantially independent of the X-ray source intensity. The material in the dummy attenuator 25 compensates, to some extent, for the X-ray tube spectrum drift. The space 27 between the body and block 26 is filled with a bag containing water so that the beam intensity received by the scintillator 28 is kept as constant as possible as it traverses the body 32, thus reducing the range of the readings which the photo multiplier 31 has to handle. The apparaus may be callibrated initially by inserting a round homogeneous body in the aperture of the block 26. FIG. 6b is a similar system but the chopper is discarded and two separate detectors are used for measuring the sources and readings through the body.

The modification of FIG. 6a which is illustrated in FIG. 7 constitutes one example of my present invention and is intended to reduce the time required to complete an examination. According to this example of my invention, a series of photo multipliers $31_1$, $31_2$ are used instead of the single photo multiplier 31 of FIG. 6. The photo multipliers have a common reference scintillator 29 and light pipe 30. Each photo multiplier has individual collimators between it and the source of X-rays 20, the collimators being denoted by the references $21_1$ and $23_1$ in the case of the photo multiplier $31_1$. With this form of the invention the oscillation of the photo multipliers and the associated collimating systems need be only a fraction of that of the apparatus shown in FIG. 6a, namely that of the sectoral angle between adjacent pairs of collimators. Photo multipliers could also be arranged slightly displaced downwards so that multiple pictures can be taken at one time. As indicated, in FIG. 8a the outputs of the photo multipliers $31_1$, $31_2$ are applied to a series of amplifiers $41_1$, $41_2$ . . . and thence to a serialiser 42 which feeds the plurality of outputs of the amplifiers in series to an analogue-to-digital converter 43. The digital output of the converter 43 is fed to a magnetic tape recorder 44 and thence to a digital computer 45 which is programmed to compute the absorption coefficients of the elements of a matrix notionally superimposed on the body 32 under examination. The co-efficients computed by the computer 45 are recorded by a further magnetic tape recorder 46 from which they are applied to a picture selector control device 47. The tape produced by the computer 45 may be replaced on the tape recorder 44, recorder 46 then being unnecessary. The output of device 47 is applied to a digital-to-analogue converter 48 and thence to a control circuit 49 which has a manual knob 50 for controlling the position of the contrast window and another manual knob 51 for controlling the width of the window. The output of the control circuit 49 is fed to a display unit 52 which includes a cathode ray tube having a screen 53. The display unit 52 is arranged to respond to the output signals of the digital computer to build up a visual representation of the section of the object under examination. The term "window" denotes the range of signal amplitudes which is applied to the unit 52 to form the display, and the unit 52 is thus such that different absorption coefficients can be displayed on a scale from black to white. The contrast window width control knob 51 enables the full scale black to white to be occupied by a small or large critical range of absorption coefficients, and the observer may vary the position of the window by manipulation of the control knob 50. FIGS. 8b, 8c and 8d illustrate the effect of varying the width and position of the window. The values of the absorption coefficients are indicated on the vertical scale in these Figures. FIG. 8b illustrates the case in which a wide window is used, that is to say in which the black/white range covers a wide range of values of absorption coefficients. If signals exceeding peak white are removed, for example by limiting, only tissue and tumour will show on the picture. However, as the absorption coefficient of tumour is only 10% greater than that of tissue both will appear as grey and it will be difficult to distinguish between them. FIG. 8c shows the effect of using a narrow window. In this case it is not possible to distinguish between bone and tumour but it is easy to distinguish tissue from both bone and tumour. If signals exceeding peak white are removed, only tissue will show up in the picture.

FIG. 8d shows the effect of altering the position of the narrow window used in FIG. 8c. The tumour now appears as grey while tissue exceeds peak black and bone exceeds peak white. Consequently if signals exceeding peak white and peak black are removed, only the tumour will show up in the picture. It can therefore be seen that by manipulation of the width control knob 51 and position control knob 50 the operator can eliminate from the final picture everything except the material which he wishes to examine. The display unit may also include means for displaying up to four representations of different sections at one time and provision may be made to enable the observer to dwell on one representation. A long after glow tube may be used the picture being replenished by a continuous backwards and forwards pass of the tape deck. The digital computer 45 may be an on line computer and may be remote from the magnetic tape recorders 44 and 46 being connected thereto by suitable lines or the like. Alternatively the magnetic tape recorders may be arranged to store information for computation and display at desired times.

In some cases it may be more convenient to have a direct display. This could employ a cathode ray tube store for storing the data in analogue form. Preferably, the tube should have large values of screen capacity so that the stored information may be interrogated without causing any significant change in its value. Such tubes are commonly used to provide "bright" radar displays. The summation and computing of values received from the cathode ray tube may be carried out by a simple accumulator and comparator operating a serial mode, and the output fed back to the cathode ray tube to give the necessary small additions to the charge built up over the screen. A digital computer would therefore be unnecessary.

In the examples of the invention which have been described, the detecting means detect the transmission of radiation through a plurality of paths which are parallel to the slice being examined. In some cases however some at least of the paths may be oblique to the slice and such oblique paths used to determine the transmission or absorption coefficients of the elements of a three dimensional matrix.

Another example of my invention will now be described with reference to FIGS. 10, 11 and 12 of the accompanying drawings.

Referring now to FIG. 10 the radiation emitted from an X-ray source 54 is formed, by means of a collimator 55, into a fan-shaped (i.e. sectoral) swath 56. The swath is incident upon a first shutter member 57 which is constructed of material opaque to the radiation from source 54. The member 57 is formed with a plurality of slit-like apertures such as 58, only eight such apertures being shown in the drawing for reasons of clarity, although in practice many more apertures are provided. The shutter 57 can be moved to and fro, (i.e. reciprocated) in the direction shown by an arrow 59, by means of a motor driven crank arrangement of which a part is shown at 60 in FIG. 10. The said crank arrangement will be more fully described hereinafter.

The radiation passing through the apertures such as 58 when the shutter member 57 is in a given position constitutes a group of equi-angularly spaced rays; the rays of each group being caused to traverse respective paths such as 61 through a region of interest 62.

A second shutter member 63, which is similar to the member 57, is disposed on the opposite side of the region of interest 62 to the member 57. The member 63 is also moveable (by means of a crank arrangement of which part is shown at 64) in the direction shown by the arrow 59 and its motion is synchronised with that of the member 57 so that apertures such as 65 can be aligned with the apertures such as 58 to form, in effect, a second collimating arrangement for the radiation.

Radiation which passes through a given one of the apertures such as 58 and also through the corresponding aperture such as 65 impinges upon a scintillator crystal such as 66, and the visible energy emitted by the crystal in response to the impinging radiation is collected, amplified, and converted into electrical signals by means of a photo multiplier tube such as 67. The electrical signals are processed substantially as described hereinbefore.

It will be observed that the provision of the pairs of spaced apertures such as 58 and 65 enables the radiation to be scanned, in the direction shown by the arrow 59, over the crystals such as 66. This expedient permits a single crystal/photomultiplier to be used for detecting the radiation passing along a respective ray path through the body which scans the sectoral angle between adjacent ray paths defined by the shutter apertures, so reducing (for a given number of paths and groups of paths) the number of crystals and photomultipliers used.

The position of the two shutter members 57 and 63 are monitored and these determine the ray path along which radiation impinges at any instant on the crystals. Thus, since the same crystal/photomultiplier combination provides an output signal for radiation passing through the region of interest along several different ray paths, it is necessary that the monitored information concerning the positions of members 57 and 63 be taken into account when the computations described hereinbefore are carried out.

It has been found advantageous to make the dimensions of the crystals such as 66 somewhat less than the total amplitude of scan in the direction of arrow 59 so that, at the extremes of scan, some overlap of the radiation upon an adjacent crystal occurs. This allows an extra reading to be taken in the adjacent crystal/- photomultiplier combination so that errors due to the junction line of the two crystals can be compensated for. This expedient also provides information to enable one crystal/photomultiplier combination to be matched to the adjacent combination for gain.

The collimator 55 includes a slit 68 which is parallel to the direction indicated by arrow 59, and a shutter 69 is provided as shown so that its blades (which are opaque to X-radiation) can be rotated, by means of a motor 70, into and out of the slit 68 so as to blank off the X-radiation at the extremity of each stroke of the reciprocating motion of shutters 57 and 63. The motor 70 is synchronised with the reciprocating motion in order to achieve the above end.

In FIG. 11, features which are similar to features of FIG. 10 have been allocated the same reference numerals. In FIG. 11 the crank arrangement for moving the members 57 and 63 in synchronism is shown in schematic form. It may be seen that the parts 60 and 64 are driven from a common motor 71 via respective couplings 72 and 73. At the left hand ends of members 57 and 63 there are provided respective crank parts 74 and 75 which have shafts which are journalled in bearings 76 and 77 respectively. The motor 71 is preferably a 50 Hz synchronous motor.

If the crank arrangement shown in FIG. 11 were used without modification, the to and fro motion of the shutter members 57 and 63 would be substantially sinusoidal, whereas it is desired that they should follow a substantially triangular wave motion. In accordance with a feature of the invention, and as shown in part in FIG. 12, the crank arrangement is modified in a way which introduces third harmonic distortion into the aforementioned sinusoidal motion, so tending to linearise the motion.

Referring now to FIG. 12, the motor 71 drives the shafts 72 and 73 both in the same rotation sense. At the upper end of shaft 73 there is provided a cross-member 78 which is fixed to the shaft 73 to form a T-piece. One end of the cross-member 78 is formed with an aperture (not shown) through which a spindle 79 is passed, the arrangement being such that the spindle 79 can rotate in said aperture. The other end of the cross-member 78 is provided with a balance weight 80.

Fixedly secured to the spindle 79 is a gear wheel 81 which is arranged to be driven around a stationary gear wheel 82 by the action of the T-piece 73, 78. The meshing of the gears on wheels 81 and 82 causes the former wheel to rotate about its own axis, thus causing spindle 79 to rotate. The spindle 79 carries at its upper end a cross-member 83 which is shaped at one end to pass through an aperture in the shutter member 63 and which is provided at its other end with a balance weight 84.

The diameter of the fixed gear wheel 82 is arranged to be twice that of the gear wheel 81 and the arrangement is such that the additional motion imparted to shutter member 63 by virtue of the rotation of gear wheel 81 introduces third harmonic distortion into the substantially sinusoidal motion which would have been produced by T-piece 73, 78 alone and thus linearises the motion of the shutter member.

The drive arrangement for the shutter member 57 can be exactly as shown in FIG. 12 apart from the fact that the dimensions of the cross-members corresponding to 78 and 83 and of the wheels corresponding to 81 and 82 are reduced.

It will be observed from FIGS. 10 and 11 that adjacent ones of the photomultipliers such as 67 are disposed along orthogonal axes. This expedient is used to facilitate the arrangement of the photomultipliers in close proximity to one another, since it will be appreciated that the crystals such as 66 are shown on an enlarged scale and that, in practice, many more than the eight crystals shown are used. It will be appreciated also that a pair of corresponding apertures is provided, one in each of the shutter members 57 and 63, for each crystal such as 66.

Referring again to FIG. 11, the apparatus including the source 54, the first collimator 55, the shutter 69 and its motor 70, the shutter members 57 and 63, the scintillator crystals 66 and the photomultipliers 67 is orbited around the region of interest 62 by means of a motor 85 driving a turntable means 86 on which all of said components are mounted. The motor 85 is preferably synchronised with the reciprocating motion of shutter members 57 and 63 so that each time the shutter members reach an extremity of their travel, the motor 85 is operative to step the turntable around through (say) 1° of rotation. By this means, if all the rays traversing the region 62 at a given angular position of the turntable 86 are referred to as a set of paths, then a corresponding set of paths is traced at each angular position of said turntable. Preferably the turntable is rotated through at least 180° for a given examination.

It will be appreciated that the radiation effects a fan-shaped sweep of the body in a planar slice thereof since the source is a virtual point source in the plane. The source may however have some extent perpendicular to the plane of sweep, since the slice may be relatively thick, or more than one slice may be examined simultaneously. Moreover, in the case where several ray paths are defined by the scanning system, in its rest position, these paths may be parallel, several virtual point sources of radiation then being required.

What I claim is:

1. A method of examining a body comprising the steps of:

generating first electrical signals each of which is a function of penetrating radiation which has travelled along a respective beam path from an origin of the radiation to a device for detecting the radiation during a respective detector sampling time interval;

where said beam paths pass through an area containing a sectional slide of a body, and where any beam path passing through the slice overlaps throughout the slice with another one of said beam paths, the cross-sectional dimensions of a beam path being small as compared to the size of the slice;

generating second electrical signals each of which is for a respective straight direction across the slice and is a function of a multiplicity of first electrical signals, said directions being distributed at least through an angle of about 180° relative to the slice;

generating third electrical signals each of which is for a respective elemental area of a picture of the slice and is a function of an accumulation of allocations, wherein each allocation is a function of the second electrical signals for directions through or adjacent the part of the slice pictured at that elemental area of the picture; and displaying a visible picture of the slice, said visible picture being a function of the third electrical signals.

2. A method as in claim 1 in which the step of displaying a visible picture of the slice comprises displaying a selected window range of display signals which are functions of said third electrical signals, where both the width and the level of said window range are operator selectable and where only display signals whose amplitudes are within the selected range are visibly displayed at any one time.

3. A method as in claim 2 in which within any given one of said sampling time intervals the radiation comes from an origin at one side of the slice, travels through the slice along radii of a sectoral-shaped spread of radiation and is received concurrently at a number of detector devices, and in which a respective first electrical signal is generated in response to the radiation received at each of the detector devices within the given sampling time interval.

4. A method as in claim 3 in which the spread of radiation coming from the origin passes, before it reaches the slice, through a block of material shaped such that the radiation along the central radius of the sectoral-shaped spread passes through a selected thickness of said material and the radiation along radii which are progressively further in angle from the central radius passes through progressively greater thicknesses of said material, and where the spread of radiation is sufficiently wide to encompass the entire slice and the radiation origin moves relative to the slice solely in an arcuate motion around the slice.

5. A method as in claim 3 in which the radiation moves around the slice and, in addition, there is relative motion between the detector devices and the origin of the radiation.

6. A method as in claim 3 in which the spread of radiation is sufficiently wide to encompass the entire slice.

7. A method as in claim 6 in which any one of said detector devices receives radiation along a given radius or given radii of the spread within one of said detector sampling time intervals and along another radius or other radii at another one of said detector sampling time intervals.

8. A method as in claim 6 in which said detector devices rotate around the slice.

9. A method as in claim 2 in which the step of generating the first electrical signals comprises providing an origin of the radiation at one side of the slice and at least one detector device at the other slice of the slice, and moving the origin and the at least one detector, as a unit, relative to the slice in a succession of linear scans, where each successive linear scan is at an angle with respect to the slice which is different from that of the preceding linear scan, and where there are many detector sampling time intervals during any one of the linear scans.

10. A method as in claim 1 in which the radiation travels through the slice along radii of a sectoral-shaped spread of radiation and is received concurrently at a number of detector devices, and the spread of radiation is sufficiently wide to encompass the entire slice.

11. A method as in claim 10 in which the origin of the radiation moves relative to the slice solely in an arcuate motion about the slice.

12. A method as in claim 11 in which the detector devices rotate about the slice.

13. A method as in claim 11 in which any given one of said detector devices receives radiation along a given radius or given radii of the spread within one of said detector sampling time intervals and along another radius or other radii at another one of said detector sampling time intervals.

14. A method as in claim 1 in which the step of generating the first electrical signals includes providing an origin of radiation at one side of the slice and at least one detector device at the other side of the slice, and moving the origin and the at least one detector relative to the slice in a succession of linear scans, where each successive linear scan comprises movement of the origin and the at least one detector along respective lines which are at angles relative to the slice different from those of the preceding linear scan and where there are many detector sampling time intervals during any one of the linear scans.

15. A method as in claim 1 in which the step of generating the first electrical signals includes providing an origin of the radiation which moves around the slice, and at least one detecting device, and causing relative motion between the origin and the at least one detector device.

16. A method as in claim 1 in which the step of generating the third electrical signals comprises the accumulation, for a given elemental area of the picture, of allocations which are functions not only of those of the second electrical signals which are for directions which go through or adjacent the part of the slice pictured at that elemental area of the picture but also of the relative positions in space of the respective directions and the last recited part of the slice.

17. A method of examining a body comprising the steps of:
generating first electrical signals each of which is a function of the penetrating radiation travelling in a three-dimensional path along a respective straight direction through a sectional slice of the body, where the paths along any two of said directions which are not separated from each other by another of said directions overlap each other throughout the slice, said directions being distributed through at least an angle of about 180° relative to the slice;
generating second electrical signals each of which is a function of a number of first electrical signals and is for a respective direction across the slice;
building up a picture of the attenuation properties of the slice relative to the penetrating radiation by accumulating, for each given elemental area of the picture, allocations depending on the second electrical signals for directions having selected geometric relationships to the part of the slice pictured at that given elemental area of the picture, and forming a tangible record of the resulting picture.

18. A method as in claim 17 in which the penetrating radiation comes from an origin which moves relative to the slice solely in an arcuate motion about the slice.

19. A method as in claim 18 wherein the step of generating the first electrical signals includes detecting the slice-attenuated radiation by means of at least one detector device which also rotates about the slice.

20. A method as in claim 19 in which the slice-attenuated radiation is concurrently detected by a number of detector devices.

21. A method as in claim 18 in which the penetrating radiation comes from an origin which rotates about the slice, and the step of generating the first electrical signals comprises detecting slice-attenuated radiation by means of at least one detector device, where there is relative motion between the radiation origin and the at least one detector device.

22. A method as in claim 17 in which the step of generating the first electrical signals comprises providing an origin of the radiation at one side of the slice and at least one detector device receiving slice-attenuated radiation, and moving the origin and the at least one detector device as a unit relative to the slice in a succession of linear scans which are at respective angles relative to the slice.

23. A method as in claim 17 in which the radiation passing through the slice is in the shape of a fan encompassing the slice, and including causing said radiation to pass through a block of material which is shaped and positioned relative to the slice such that the radiation passing through the center of the slice first passes through a selected thickness of the material while the radiation passing through parts of the slice which are progressively further away from the slice center passes through progressively greater thicknesses of said material.

24. A method as in claim 17 in which, for each given elemental area of the picture, each given one of said allocations is a function not only of the second electrical signal for a respective direction but also of the relative positions in space of the last recited direction and the part of the slice pictured at that given elemental area of the picture.

25. A method comprising the steps of:
irradiating a sectional slice of a body with x-rays;
receiving the x-rays emerging from the slice during each of a succession of detector sampling time intervals and generating, in response, first electrical signals each of which is a function of the x-rays which have travelled through the slice within a respective path during a respective detector sampling time interval, each respective one of said paths having a geometric center line which is straight, where the paths having center lines which are not separated from each other by another center line of a path overlap each other throughout the slice, and where said center lines are distributed at least throughout an angle of about 180° relative to the slice, and every elemental part of the slice is intersected by a number of said paths;
deriving, from said first electrical signals, second electrical signals which have a positional correspondence to said center lines, where each second electrical signal is a function of a number of said first electrical signals;
building up an x-ray picture of the slice by accumulating, for each given elemental area of the picture, allocations which are functions of the second electrical signal which have a positional correspondence with first electrical signals which are functions of the x-rays that have travelled along beam paths intersecting the elemental part of the slice pictured at said given elemental area of the picture, and forming a visual representation of said x-ray picture.

26. A method as in claim 25 in which the step of building up the x-ray picture includes accumulating, for each given elemental area of the picture, allocations each of which is a function of a second electrical signal which has a selected positional correspondence with a first electrical signal which in turn is a function of x-rays that have travelled along a selected beam path intersecting the elemental part of the slice pictured at said given elemental area of the picture as well as of the relative positions in space of the last recited beam path and the last recited part of the slice.

27. A method as in claim 25 in which the irradiating step comprises irradiating the slice with a fan-shaped spread of x-rays.

28. A method as in claim 27 in which said fan-shaped spread of x-rays is sufficiently wide to encompass the entire slice.

29. A method as in claim 28 in which the step irradiating comprises first passing the x-rays through a block of material such that the center of the fan-shaped spread passes through a selected thickness of the material and the sides of the spread of x-rays pass through progressively greater thicknesses of said material.

30. A method as in claim 28 in which the receiving step comprises concurrently receiving the x-rays at a number of detector devices which move solely arcuately, rather than linearly, about the slice.

31. A method as in claim 28 in which the irradiating step comprises irradiating the slice with x-rays coming from an origin which rotates about the slice, and the receiving step comprises concurrently receiving the x-rays at a number of detector devices, and wherein there is relative motion between the origin and the detector devices.

32. A method comprising the steps of:
irradiating a sectional slice of an object with x-rays coming from an x-ray origin moving relative to the slice;
receiving x-rays emerging from the slice and generating, in response, first electrical signals where:
(i) each respective first electrical signal is generated in response to the x-rays received by a respective detector device during a respective detector sampling time interval;
(ii) the x-ray origin and each respective detector device occupy respective positions during each respective detector sampling time interval, and all of the x-rays which go directly from the x-ray origin to a respective detector device during a detector sampling time interval travel within a beam path bound at its longitudinal ends by the outlines of the last recited respective positions of the x-ray origin and detector device; and
(iii) any two beam paths, whether or not they exist at the same time, which are not separated from each other by another beam path spatially overlap with each other throughout the slice;
converting said first electrical signals to second electrical signals, where each second electrical signal is a function of a respective multiplicity of the first electrical signals, and each second electrical signal is associated with a respective direction across the slice, said directions being distributed at least through an angle of about 180° relative to the slice;
converting the second electrical signals into third electrical signals, where each third electrical signal is associated with a respective small area of an x-ray picture of the slice and is a function of those second electrical signals which are associated with directions passing through the part of the slice pictured at said small area of the picture; and
converting said third electrical signals into a visible x-ray picture of the slice.

33. A method as in claim 32 in which the irradiating step comprises irradiating the slice with a spread of x-rays which is sufficiently wide to encompass the entire slice.

34. A method as in claim 33 in which the x-ray origin moves relative to the slice solely in an arcuate motion about the slice.

35. A method as in claim 34 in which the step of receiving x-rays comprises receiving the x-rays by means of at least one x-ray detector device, and where there is relative motion between the x-ray origin and the at least one detector device.

36. A method as in claim 34 in which the step of receiving the x-rays comprises concurrently receiving the x-rays at a multiplicity of respective detector devices, and in which both the x-ray origin and the detector devices rotate about the slice.

37. A medical diagnostic method of examining a patient and building up and displaying a two-dimensional picture of the x-ray absorption of the elements into which a substantially planar slice of the patient is divided by a finite Cartesian notional matrix superimposed on the slice, comprising:

producing x-radiation originating at an origin scanning around the patient, said x-radiation passing through the patient while the origin scans at least half way around the patient, and detecting the x-radiation and producing electrical signals corresponding to the absorption suffered by the x-radiation in passing through the patient along beam paths which are in or substantially in the slice, at least some of these beam paths intersecting each other and the neighboring beam paths overlapping each other;

providing signal receiving meshes corresponding to the slice elements and allocating, for each given beam path, to the meshes corresponding to the slice elements through which the given beam path passes, allocations determined by a correction signal weighted in accordance with the relative disposition of the given beam path and the slice elements through which the given beam path passes, said correction signal being determined by modifying the electrical signal corresponding to the given beam path in accordance with other electrical signals, corresponding to beam paths which pass through slice elements other than those through which the given beam path passes, and accumulating said allocations to each signal receiving mesh to thereby build up said picture; and displaying the so accumulated allocations to the signal receiving meshes to thereby display said two-dimensional picture of the x-ray absorption of the elements of the patient slice.

38. A medical diagnostic method as in claim 37 in which the x-radiation fans out from said origin into a sectoral-shaped swath of radiation which is wide enough to span the entire patient slice, and the steps of detecting the x-radiation and producing said electrical signals comprise using a plurality of separate detecting devices each viewing the radiation origin along a respective beam path which is within said swath of radiation and is angularly spaced from the beam paths along which the other detecting devices view the radiation origin at the same time.

39. A medical diagnostic method as in claim 38 including causing relative motion between the radiation origin and the detecting devices to cause each detecting device to view the radiation origin along beam paths which are at different angles relative to the mean angle of the swath of radiation at different positions of the radiation origin with respect to the patient slice in the course of said scanning of the radiation origin around the patient.

40. A medical diagnostic method as in claim 37 in which the radiation forms a beam wide enough to span the entire patient slice and said scanning of the origin comprises rotation of the radiation origin about the patient, and said steps of detecting the x-radiation and producing said electrical signals comprise using at least one detecting device viewing the radiation, during rotation of the origin about the patient, along beam paths which are within the beam of x-radiation but are angularly spaced from each other within said beam and are distributed throughout the entire patient slice.

41. A medical diagnostic method as in claim 37 in which the x-radiation fans out along divergent beam paths from the radiation origin, and the steps of detecting the x-radiation and producing said electrical signals comprise using a plurality of separate detecting devices each viewing the radiation origin along a different one of said divergent beam paths and scanning the detecting devices relative to the patient, in synchronism with said scanning of the radiation origin, in a first scanning motion causing sweeping the slice with said divergent beams along a direction generally transverse to the propagation direction of the x-radiation and in a second scanning motion causing rotation of said divergent beams about an axis transverse to and intersecting the slice, to thereby distribute said divergent beams over the entire patient slice.

42. A medical diagnostic method as in claim 37 in which the x-radiation fans out from the radiation origin, in the plane of the slice, and the steps of detecting the x-radiation and producing said electrical signals comprise using a plurality of separate detecting devices viewing the radiation origin, at any one position thereof with respect to the patient slice, along a set of angularly spaced beam paths diverging from the radiation origin along said radiation fanning out therefrom and spaced from each other when passing through the patient to leave gaps between adjacent beam paths of a set, and including scanning the detecting devices relative to the patient in synchronism with said scanning of the radiation origin to cause the beam paths of each set to be at the gaps of another set of beam paths.

43. A medical diagnostic method of examining a patient comprising:

producing x-radiation originating at an origin scanning around the patient, said radiation fanning out from said origin into a sectoral-shaped swath of radiation which is wide enough to span an entire slice of the patient and passes through the patient, in the slice thereof, while the origin scans at least half way around the patient, and producing electrical signals corresponding to the absorption suffered by the x-radiation in passing through the patient along beam paths which are in, or substantially in, the slice, at least some of these beam paths intersecting each other and the neighboring beam paths overlapping each other, said step of producing said electrical signals comprising using a plurality of separate devices for detecting x-radiation each of which receives x-radiation from the origin emerging from the patient at a given time along a respective beam path which is within the swath of x-radiation and is angularly spaced from the beam paths along which other detecting devices receive x-radiation from the origin at the same time; and processing said electrical signals to build up and display a two-dimensional picture of a characteristic of said slice relative to the x-radiation.

44. A medical diagnostic method as in claim 43 including causing relative motion between the radiation origin and the detecting devices to cause each detecting device to receive x-radiation from the origin along beam paths which are at different angles relative to the mean angle of the swath of radiation at different positions of the radiation origin with respect to the patient in the course of said scanning of the radiation origin around the patient.

45. A medical diagnostic method of examining a patient comprising:

producing x-radiation originating at an origin scanning around the patient, said x-radiation forming a beam wide enough to span an entire slice of the patient and said beam passing through the patient, in said slice thereof, while the origin scans at least half way around the patient, and detecting the x-radiation and producing electrical signals corresponding to the absorption suffered by the x-radiation in passing through the patient along narrow beam paths which are within said wide beam and are in, or substantially in the slice, at least some of said narrow beam paths intersecting each other and the neighboring beam paths overlapping each other in the slice, said steps of detecting the x-radiation and producing said electrical signals comprising using at least one detecting device viewing the radiation origin at different times along narrow beam paths which are within the wide beam of x-radiation but are angularly spaced from each other within said wide beam, where the entire patient slice is swept with said narrow beam paths; and building up and displaying a two-dimensional picture of a characteristic of said slice relative to the x-radiation from said electrical signals.

46. A medical diagnostic method of examining a patient and building up and displaying a two-dimensional picture of the x-ray absorption of the elements into which a planar or a substantially planar slice of the patient is divided by a finite Cartesian matrix notionally superimposed on the slice, comprising:

producing x-radiation originating at an origin scanning around the patient, said radiation passing through the patient while the origin scans at least half way around the patient, and detecting the x-radiation and producing electrical signals corresponding to the absorption suffered by the x-radiation in passing through the patient along beam paths at least some of which intersect each other, with neighboring beam paths overlapping each other;

providing signal receiving meshes corresponding to the slice elements and making a succession of signal allocations to each mesh to thereby build up said picture of the x-ray absorption of the slice elements, each signal allocation to any one mesh being responsive to the electrical signal corresponding to a beam path passing through the slice element which corresponds to that mesh modified by electrical signals corresponding to beam paths not passing through that slice element, a so modified electrical signal being derived for each individual one of said electrical signals and being allocated to all of the meshes corresponding to slice elements through which the beam path corresponding to the individual electrical signal passes, in weights determined by the relative disposition of the last recited beam path and slice elements, each so modified and weighted signal constituting a signal allocation to a mesh, and the signal allocations to a mesh being accumulated thereby to thereby build up said picture; and displaying said accumulations of signal allocations to thereby display said two-dimensional picture of the x-ray absorption of the patient slice.

47. A medical diagnostic method as in claim 46 in which the steps of detecting the x-radiation and producing said electrical signals comprise producing electrical signals corresponding to beam paths each of which is substantially wider in cross-section than a slice element.

48. A medical diagnostic method as in claim 47 in which the steps of detecting the x-radiation and producing said electrical signals comprise producing electrical signals for beam paths which are substantially greater in number than the number of the slice elements.

49. A medical diagnostic method as in claim 48 in which the displaying step comprises selectively displaying only x-ray absorptions which are within a selected range from a selected central value.

50. A method of examining a patient comprising:

irradiating an area which includes a transverse slice of the patient with penetrating radiation propagating along many different but substantially coplanar directions distributed throughout the area and generating respective signals related to the radiation detected after leaving said area along the respective directions;

using said signals to build up a picture of the slice by an apparatus-implemented process in which (i) each of substantially all of said signals contributes to substantially the entire picture and (ii) substantially the entire picture receives contributions from one group of said signals and then from another as it is being built up;

wherein each group of signals is related to a group of directions distributed substantially uniformly through substantially the entire slice, and wherein said picture has a contrast range corresponding to the range at least from soft tissue through bone; and displaying a visual representation of said picture which selectively shows only a portion of said contrast range within a selectable window width at a selectable window position.

51. A method of examining a patient as in claim 50 in which the irradiating step comprises irradiating the area with a sectoral-shaped beam of said penetrating radiation, and the generating step comprises detecting the radiation leaving said area at a given time with a number of detector devices each being separate and distinct from other detecting devices and each receiving at the time radiation which has travelled within a respective subsector of said sectoral-shaped beam.

52. A method of examining a patient as in claim 51 in which said sectoral-shaped beam of radiation is wide enough to encompass the entire slice.

53. A method of examining a patient as in claim 52 in which the origin of the sectoral-shaped beam of radiation moves around the patient in a continuous circular motion and in which there is relative motion between said origin and said detector devices.

54. A method of examining a patient as in claim 51 in which said apparatus-implemented process includes accumulating, for each elemental area of the picture, allocations each of which depends on a signal for a direction which passes through or near the elemental part of the slice imaged at said elemental area of the picture, on the distance between the center of the last recited elemental part of the slice and the last recited direction, and on other signals which are for other directions, and wherein, all other things being equal, a lesser allocation is made for a greater distance than for a lesser distance.

55. A method of examining a patient comprising:
irradiating an area which includes a transverse slice of the patient with penetrating radiation propagating along many different but substantially coplanar directions distributed throughout the area, and generating respective signals related to the radiation detected after leaving said area along the respective directions;
subjecting said signals to an apparatus-implemented process to build up a picture of the slice by a sequence of steps in which (i) each of substantially all of said signals contributes to substantially the entire picture and (ii) substantially the entire picture receives contributions based on one group of said signals and then receives and accumulates successive contributions based on successive other groups of said signals as it is being built up; and
producing and displaying a tangible visible representation of at least a portion of said picture.

56. A method of examining a patient as in claim 55 in which the irradiating step comprises irradiating the area with a sectoral-shaped spread of penetrating radiation from angular positions which are distributed substantially uniformly at least through an angle of about 180° around the patient, and the generating step includes receiving the radiation leaving said area concurrently at a number of detector devices each of which at a given time views at least a part of a respective subsector of said sectoral-shaped spread of radiation.

57. A method of examining a patient as in claim 56 in which the detector devices move at least about halfway around the patient.

58. A method of examining a patient as in claim 56 in which the radiation within a given subsector of said sectoral-shaped spread of radiation irradiates different detector devices at different times.

59. A method of examining a patient as in claim 52 in which said process includes the step of accumulating respective successive allocations for each respective elemental area of the picture, each allocation depending on (i) the respective signal for a direction which passes through or near the elemental slice portion imaged at the respective elemental area of the picture, (ii) the distance between the center of the last recited elemental slice portion and direction, and (iii) other respective signals which are for respective other directions; wherein all other things being equal, a lesser distance results in a higher allocation than a greater distance.

60. A method of examining a patient as in claim 56 including the step of generating, concurrently with the generation of said respective signals, reference signals which provide reference for said respective signals for the purpose of making the respective signals substantially independent of the intensity of the origin of said penetrating radiation.

61. A method of examining a patient as in claim 55 including the step of generating, concurrently with the generation of said respective signals, reference signals which provide reference for said respective signals for the purpose of making the respective signals substantially independent of the intensity of the origin of said penetrating radiation.

62. A method of examining a patient as in claim 61 in which the generating step comprises generating respective signals each of which is related to the radiation which has travelled through said area within a respective three-dimensional beam path associated with the respective direction, and wherein the width of beam paths which are spatially adjacent, though they may exist at different times, is greater than the distance therebetween so that overlapping occurs therebetween.

63. A method comprising the steps of:
irradiating a transverse section of a body with penetrating radiation from many different directions, detecting body-attenuated radiation to produce signals related thereto for many respective directions, correcting the signals on the basis of contributions from others of said signals to enhance their usefulness for building an accurate picture of said section, and building up a picture of said transverse section by cumulatively allocating the corrected signals to picture strips which are along the respective directions corresponding to the respective corrected signals.

64. A method as in claim 63 in which the irradiating and detecting steps comprise scanning the body with a unit comprising a source of the penetrating radiation and means for detecting the body-attenuated radiation which are fixed relative to each other, said scanning comprising moving the unit laterally across the body, then rotating it about the body, then moving it back across the body, etc., so that said directions are distributed through at least an angle of about 180° around the body.

65. A method as in claim 63 in which the irradiating step comprises moving a source of the penetrating radiation in a continuous rotational motion about the body, said source producing a sectoral-shaped swath of penetrating radiation which is wide enough to encompass the entire transverse section of the body.

66. A method as in claim 65 in which the detecting step comprises moving about the body, in synchronism with the source, a number of devices for detecting body-attenuated penetrating radiation.

67. A method as in claim 65 in which the detecting step comprises detecting body-attenuated radiation with a number of detecting devices such that there is relative motion between the source of the penetrating radiation and the detecting devices.

68. A method as in claim 63 where said picture is a picture of the x-ray attenuation properties of said transverse section of the body, and including the step of selectively displaying said picture by showing thereon only the attenuation properties falling within a selected window width which is at a selected window position.

* * * * *